United States Patent
Riggenmann

(10) Patent No.: US 8,899,101 B2
(45) Date of Patent: Dec. 2, 2014

(54) APPARATUS FOR SAMPLE HANDLING

(75) Inventor: Hansjürgen Riggenmann, Diessen (DE)

(73) Assignee: Riggtek GmbH, Munich (DE)

( * ) Notice: Subject to any disclaimer, the term of this patent is extended or adjusted under 35 U.S.C. 154(b) by 613 days.

(21) Appl. No.: 13/024,595

(22) Filed: Feb. 10, 2011

(65) Prior Publication Data

US 2011/0197661 A1  Aug. 18, 2011

(30) Foreign Application Priority Data

Feb. 12, 2010 (DE) .................... 20 2010 002 289 U

(51) Int. Cl.
| | | |
|---|---|---|
| G01N 30/16 | (2006.01) | |
| G01N 33/15 | (2006.01) | |
| G01N 35/10 | (2006.01) | |
| G01N 13/00 | (2006.01) | |

(52) U.S. Cl.
CPC ............ *G01N 33/15* (2013.01); *G01N 35/1065* (2013.01); *G01N 35/1083* (2013.01); *G01N 2013/006* (2013.01)
USPC ......................... 73/61.55; 73/864.01; 356/246

(58) Field of Classification Search
CPC . G01N 2013/006; G01N 33/15; G01N 13/00; G01N 35/1065; G01N 30/24; G01N 30/20; B01I 7/00; C12Q 1/686; C12Q 2565/629
See application file for complete search history.

(56) References Cited

U.S. PATENT DOCUMENTS

| | | | |
|---|---|---|---|
| 5,589,649 A | | 12/1996 | Brinker |
| 5,957,669 A | * | 9/1999 | Parikh et al. .................. 417/362 |
| 6,948,389 B2 | | 9/2005 | Brinker |
| 2003/0152493 A1 | * | 8/2003 | Lefebvre ....................... 422/100 |
| 2003/0155371 A1 | | 8/2003 | Collasius et al. |
| 2003/0217608 A1 | * | 11/2003 | Brinker et al. ............. 73/864.34 |
| 2007/0065305 A1 | * | 3/2007 | Budde et al. .................. 417/395 |
| 2007/0243600 A1 | * | 10/2007 | Lair et al. .................. 435/287.2 |
| 2009/0079976 A1 | * | 3/2009 | Cunningham et al. ........ 356/246 |

FOREIGN PATENT DOCUMENTS

| | | |
|---|---|---|
| DE | 69223875 T2 | 4/1998 |
| DE | 60221984 B1 | 5/2008 |
| EP | 0527059 B1 | 2/1993 |
| EP | 1261428 B1 | 4/2002 |
| EP | 1399724 B1 | 3/2004 |

* cited by examiner

*Primary Examiner* — Peter Macchiarolo
*Assistant Examiner* — Mohammed Keramet-Amircola
(74) *Attorney, Agent, or Firm* — Lathrop & Gage LLP; Anthony J. Janiuk

(57) ABSTRACT

A sampler (10), in particular for use in testing the dissolution behavior of pharmaceutical products, wherein the sampler (10) comprises: a vial holder (20) for accommodating a plurality of vials (22a, 22b); a sampling needle assembly (30) with a plurality of sampling needles, wherein the sampling needle assembly (30) and the vial holder (20) may be moved relative to one another in such a way that the sampling needles of the sampling needle assembly (30) may be inserted into the vials of the vial holder (20); and a pump unit (40) with a plurality of diaphragm pumps (42a, 42b) which are designed to convey a fluid via the sampling needle assembly to the vials in the vial holder (20) and to withdraw a fluid therefrom.

6 Claims, 3 Drawing Sheets

APPARATUS FOR SAMPLE HANDLING

CROSS-REFERENCE TO RELATED APPLICATIONS

This application claims priority of German Patent Application No. DE 20 2010 002 289.4, filed Feb. 12, 2010, which is incorporated herein by reference in its entirety.

FIELD OF THE INVENTION

The present invention concerns an apparatus for sampling and for sample handling, also known as a sampler or autosampler. The apparatus according to the invention is especially suitable for use in testing the dissolution behavior of pharmaceutical products.

BACKGROUND OF THE INVENTION

Apparatuses and methods are known for simulating the dissolution behavior of pharmaceutical products in the human digestive system and for obtaining information about this process. Conventional apparatuses for testing the dissolution behavior of dosages of pharmaceutical products have a dissolution unit with multiple dissolution vessels, in each of which is placed a test solution and a dosage of a pharmaceutical product to be tested, such as a tablet. After a tablet, for example, has been placed in the test solution in a dissolution vessel in which the conditions prevailing in the human digestive system are to be simulated, a stirring element in the test solution is rotated at a specified rate for a specified duration. An example of such a dissolution unit is shown in U.S. Pat. No. 5,589,649.

In order to track the progress of the dissolution behavior over time, samples of a respective test solution in which the dosage of the pharmaceutical product dissolves are taken or withdrawn from a respective dissolution vessel at certain time intervals and are conveyed to an analytical instrument. Systems are known for this process, which are commonly referred to as autosamplers or samplers, in order to automate various aspects of withdrawing samples from the test solution and conveying the samples that have been withdrawn or taken to an analytical instrument. In such systems, samples and other fluids are conveyed by pumps through tubing lines. Samplers are known which allow the testing of several dosages of a pharmaceutical process at the same time, in which samples of test solution with the dosage of the pharmaceutical product dissolving therein are withdrawn from each dissolution vessel a number of times. In prior art samplers, the withdrawn samples are delivered to collection receptacles, such as test tubes or vials, for temporary storage prior to analysis. The samplers may also automatically transfer samples from the collection receptacles to an analytical instrument at appropriate times for analysis.

Samplers typically have a rack that can hold a group of collection receptacles for keeping collected samples, and a head at which a set of lines terminates, the lines each being connected to a pump to serve a particular dissolution vessel. The head and the group of collection receptacles can be moved and positioned relative to one another so that a particular withdrawn sample can be delivered to a particular collection receptacle for storage. Prior art systems may also be designed to flush, wash, and purge the tubing lines, and to replace the test solution in which a dosage of the pharmaceutical product is dissolving that has been withdrawn from the dissolution vessels with fresh test solution, which is known as media replacement, and/or to return to the dissolution vessels a portion of the withdrawn test solution that is not delivered to the collection receptacles, which is known as media recycling.

In prior art samplers, the pumps for transporting fluids are implemented as tubing pumps or as piston pumps.

In a sampler with tubing pumps or peristaltic pumps, respective elastic tubing sections of the lines are mechanically deformed or compressed by means of a motor in such a manner that the medium to be transported is forced through the tubing section, and thus through the line. In this context, the transport can be bidirectional, which is to say that the medium can be transported along the line in both directions. The intake and delivery pressure of a tubing pump is very limited, however, and the metering precision depends strongly on the back pressure and the operating life or service life. Furthermore, the reliability of delivery decreases with increasing operating life or life time of a tubing pump, since the tubing sections that are peristaltically compressed can stick together, for example, and thus hamper the flow of fluid.

In some prior art samplers, piston/syringe pumps are used instead of tubing pumps, since they operate with greater precision and reliability than tubing pumps. With valves at the inlet and outlet, bidirectional fluid transport can also be achieved. A sampler with a pump unit that includes piston/syringe pumps is described in U.S. Pat. No. 6,948,389. The pump unit described in U.S. Pat. No. 6,948,389 has eight piston pumps, each with a piston that is movable in a cylindrical pump element. The lower ends of the pistons are secured to a flange which, when raised and lowered by a mechanism driven by a motor, moves the pistons upward and downward within the cylindrical pump elements.

Samplers with piston/syringe pumps are relatively complex in technical terms, and because of the relatively large dwell volume (which is likewise known from HPLC to those skilled in the art as the volume that must be pumped until the fresh medium at the outlet of the pump system has a content of approximately 72%), and because of the fact that the FIFO principle (i.e., "first in-first out") cannot be implemented with such samplers, they are not well suited for media undergoing change, such as is the case for the change in concentration of the test solution with the dosage of the pharmaceutical product dissolving therein. Furthermore, when the piston moves within the cylindrical pump element, the friction of the piston seal on the inner surface of the cylindrical pump element, which is often made of glass, produces abraded particles, which get into the sample and can adversely affect the measurements, such as fluorescence detection, at the analytical instrument. Finally, the piston seals of piston/syringe pumps are subject to severe wear, so that they need to be serviced and replaced frequently.

The object of the present invention is thus to provide an improved sampler that does not exhibit the disadvantages described above.

SUMMARY OF THE INVENTION

The problems that beset the prior art can be solved with an improved sampler according to claim 1. The sampler according to the invention essentially comprises a vial holder for accommodating a plurality of vials and a sampling needle assembly with a plurality of sampling needles. In this solution, the sampling needle assembly and the vial holder may be moved relative to one another in such a way that the sampling needles of the sampling needle assembly may be inserted into the vials of the vial holder. The sampler additionally comprises a pump unit with a plurality of diaphragm pumps which are designed to convey a fluid via the sampling needle assembly to the vials in the vial holder and to withdraw a fluid therefrom.

According to a preferred embodiment, the diaphragm pumps have one active or controllable valve each at their fluid inlet and their fluid outlet so that bidirectional transport can be implemented. Preferably, the valves are solenoid valves. Preferably, a small stroke volume of the diaphragm pumps also makes it possible to implement the FIFO principle in the pumping.

According to a preferred embodiment, the sampler additionally comprises a control unit that is designed to move the sampling needle assembly and the vial holder relative to one another, and to drive the diaphragm pumps of the pump unit individually. Preferably, the control unit is designed to move the sampling needle assembly and the vial holder relative to one another in such a way that, as the vials of the vial holder are filled, the tips of the sampling needles in the sampling needle assembly follow the liquid level in the vial.

Additional advantageous embodiments are defined in the additional subclaims.

BRIEF DESCRIPTION OF THE DRAWINGS

The following figures present preferred exemplary embodiments of a sampler, in particular for use in testing the dissolution behavior of pharmaceutical products, and are used to explain the invention.

DETAILED DESCRIPTION OF PREFERRED EMBODIMENTS

Figure 1:
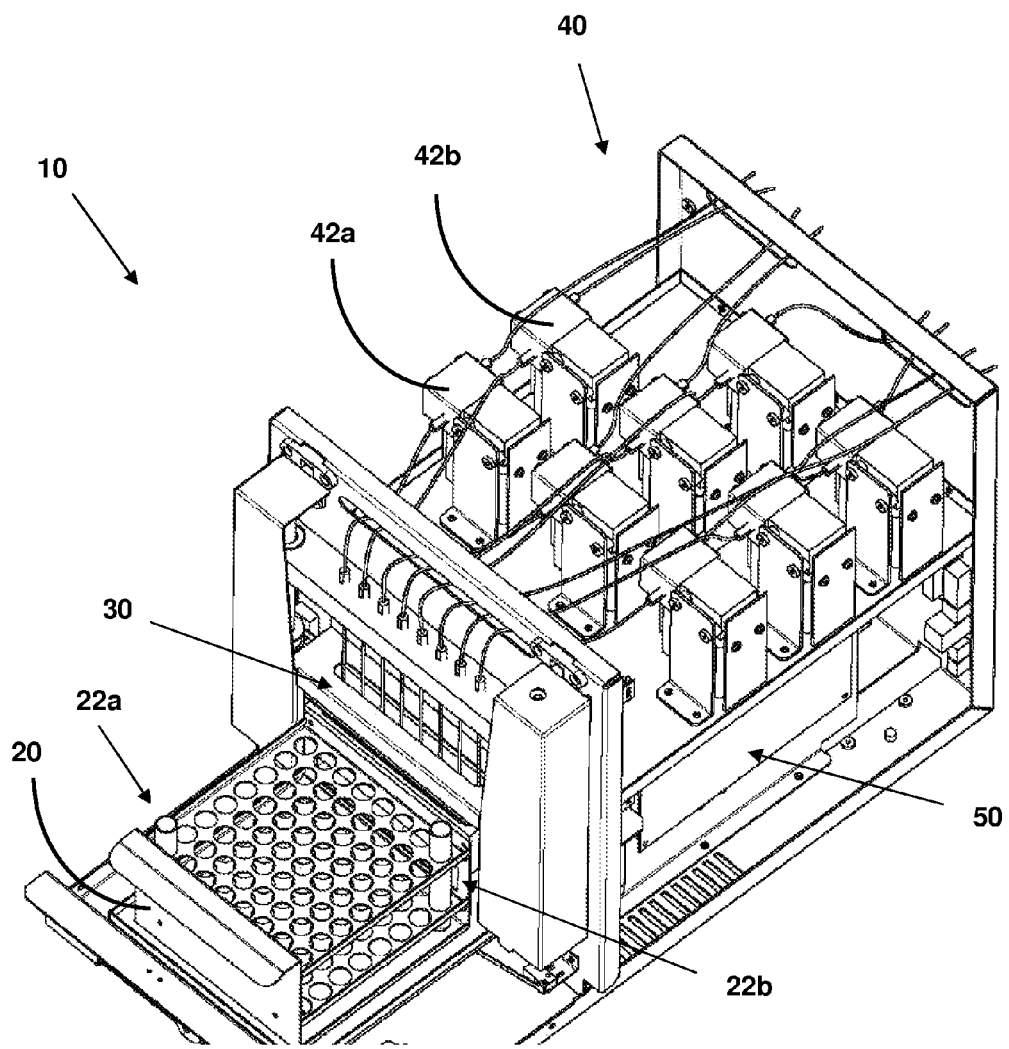
FIG. 1 shows a perspective view of a sampler according to a preferred embodiment of the invention, in particular for use in testing the dissolution behavior of pharmaceutical products.

FIG. 1 shows a sampler 10 according to a preferred embodiment of the invention, which is suitable, in particular, for use in testing the dissolution behavior of pharmaceutical products. The sampler 10 comprises a vial holder (or vial rack) 20, which is designed to accommodate a plurality of vials. Shown by way of example in FIG. 1 are two vials 22a, 22b, located in the first and last rows in the vial holder 20. In the case of the sampler 10 in FIG. 1, the vial holder 20 can accommodate up to 8×8=64 vials in a square arrangement.

Above the vial holder 20, a linear sampling needle assembly 30 with multiple sampling needles is provided so as to be movable such that the sampling needle assembly 30 can move vertically and horizontally relative to the vial holder 20, in order to insert the sampling needles of the sampling needle assembly 30 into each of the vials located in the vial holder. Naturally, for the purpose of this relative motion it is also possible to design the vial holder 20 to be movable either alone or in addition. In the embodiment shown in FIG. 1, the vial holder 20 can accommodate eight vials per row, with a total of eight rows being provided, and preferably one of these rows being used as temporary storage ("waste"), as described in greater detail below, for the flush volume of a fluid channel consisting of dissolution vessel, pump, and sampling needle. In such a case, seven rows of 8 vials each remain for sampling.

The sampler 10 additionally comprises a pump unit 40, which in the embodiment shown in FIG. 1 has eight membrane/diaphragm pumps, two of which are labeled with the reference numbers 42a, 42b by way of example. In a membrane/diaphragm pump, it is advantageous that the fluid being pumped is protected by the membrane from damaging effects of the drive. Generally, the deflection of the membrane is accomplished hydraulically, pneumatically, or mechanically. Preferably, the membrane/diaphragm pumps 42a, 42b of the pump unit 40 are equipped at their respective fluid inlet and fluid outlet with an active or controllable valve, preferably a solenoid valve. The two solenoid valves of each membrane/diaphragm pump of the pump unit 40 are driven by the control unit 50 of the sampler 10 in such a way that bidirectional pumping can be implemented. Preferably, the flow rate delivered by the membrane/diaphragm pump of the pump unit 40 is determined by the stroke frequency and by partial utilization of the intake or discharge stroke. The advantages of a membrane/diaphragm pump include the following: high metering precision, higher intake and delivery pressure, low dwell volume, chemically inert, no wearing parts, long life, low maintenance cost.

Figure 2A:
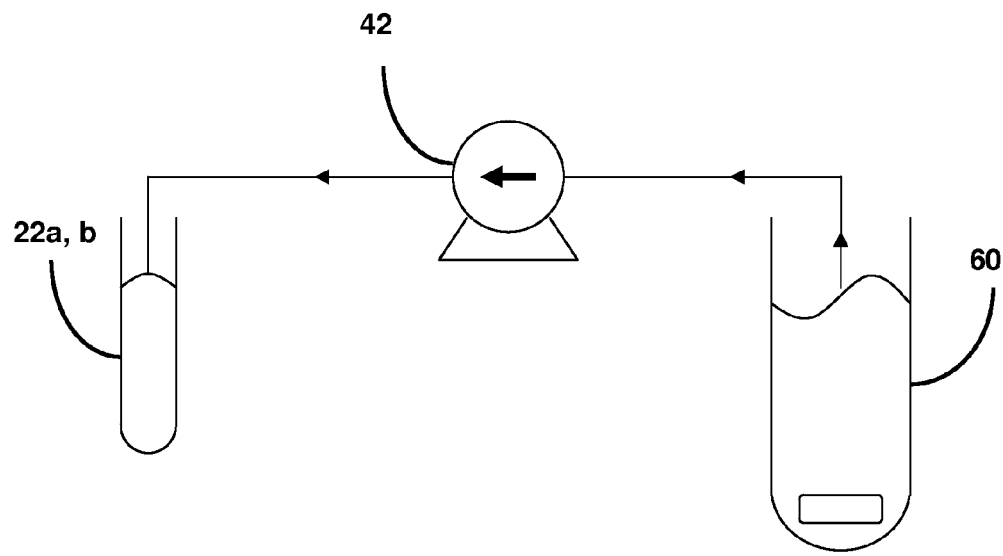
FIGS. 2a and 2b schematically show the fluid paths for testing the dissolution behavior of pharmaceutical products, which are implemented in part by the inventive sampler from FIG. 1.
Figure 2B:
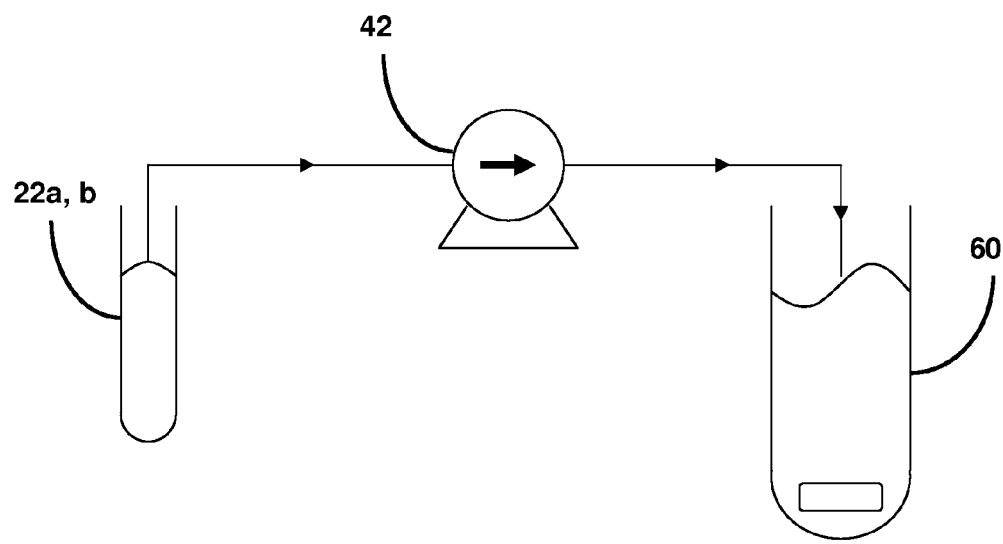

Preferably the sampler according to the invention 10 can be operated as follows, with a bidirectional fluid path being shown by way of example in FIGS. 2a and 2b.

One fluid connection of each of the membrane/diaphragm pumps of the pump unit 40 stands in fluid communication with one dissolution vessel each, for example a dissolution vessel 60, in which a solid dosage form, for example a tablet or a capsule, is being dissolved with stirring in a medium, for example the equivalent of gastric juice or intestinal juice. Generally, the dissolution process takes anywhere from a few minutes to a few hours. In addition, the membrane/diaphragm pump, which is labeled with the reference number 42a in FIGS. 2a and 2b by way of example, of the pump unit 40 of the sampler 10 is driven by the control unit 50 of the sampler 10 in such a way that samples are drawn from the respective dissolution vessel 60a according to a predetermined time schedule. Preferably the FIFO principle is implemented here. Within the scope of the present invention, the FIFO principle ("first in-first out") means that the "front" part of the fluid volume to be conveyed at the pump inlet is discharged first at the pump outlet while the "back" part of the fluid volume to be conveyed at the pump inlet is discharged last and not, as is often the case in the prior art, discharged first or mixed in the pump with the "front" part of the fluid volume to be conveyed.

A first part of the volume is used for flushing and conditioning the fluid path, and is placed in the waste vials in the vial holder 20, for example the vial 22b. So that the flushing fluid does not drop down from above and does not splash the walls of the vials, the sampling needles of the sampling needle assembly are made to follow the fill level in the vials, so that only the needle tip is wetted and, at the same time, flushed.

Starting at the scheduled time for sampling, a row of vials in the vial holder 20 is moved beneath the sampling needle assembly 30. Taking the dwell volume into account, the sample fluid flows are delivered by the membrane/diaphragm pumps, e.g. the membrane/diaphragm pump 42a, of the pump unit 40 of the sampler 10, filling the vials with the sample fractions via the sampling needles, in order to collect the sample fraction there. During this process, too, the needles are made to follow the fill level so that only the needle tip is wetted. This minimizes carry-over of the sample into the next sampling pass.

After the sample filling, the vial holder 20 with the waste vials is moved back under the sampling needle assembly 30.

The needles are moved downward until the needle tips dip into the fluid. Now the flushing fluid is pumped in return direction from the waste vials back into the dissolution vessels with the membrane/diaphragm pumps of the pump unit 40, as is shown schematically in FIG. 2b. During this process, the needles are made to continuously follow the dipping depth, so that they are not unnecessarily contaminated, and thus contribute only minimally to sample carry-over. Finally, the lines or tubing are emptied completely. With the small interior diameters of the tubing, very high fluidic resistances can arise if small sections of fluid are introduced in alternation with air bubbles. In an advantageous manner, the membrane/diaphragm pumps of the pump unit 40 can each generate a sufficiently high suction pressure to empty the tubes reliably.

Figure 3A:
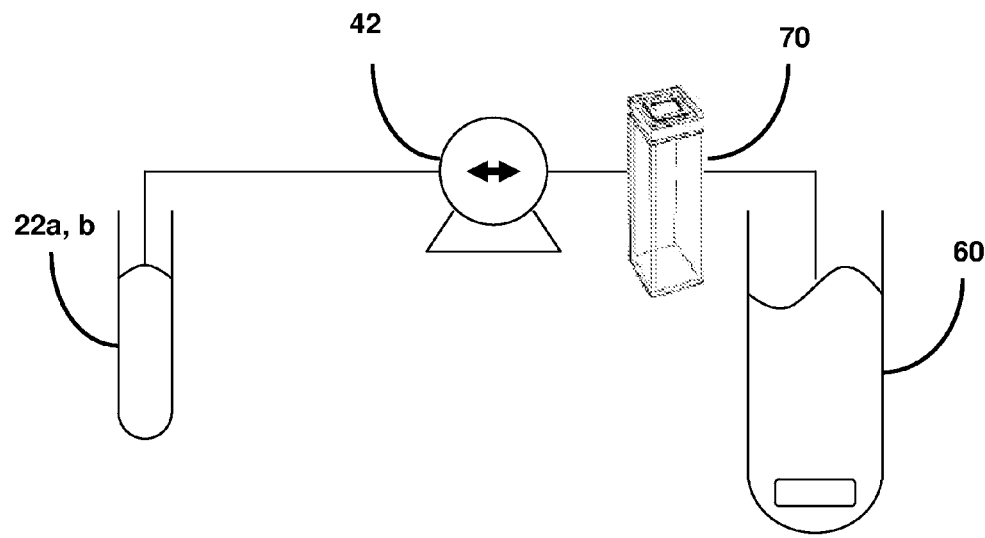
FIGS. 3a and 3b schematically show the fluid paths with a photometer measuring cell or a chromatography injection loop according to preferred embodiments of the invention.
Figure 3B:
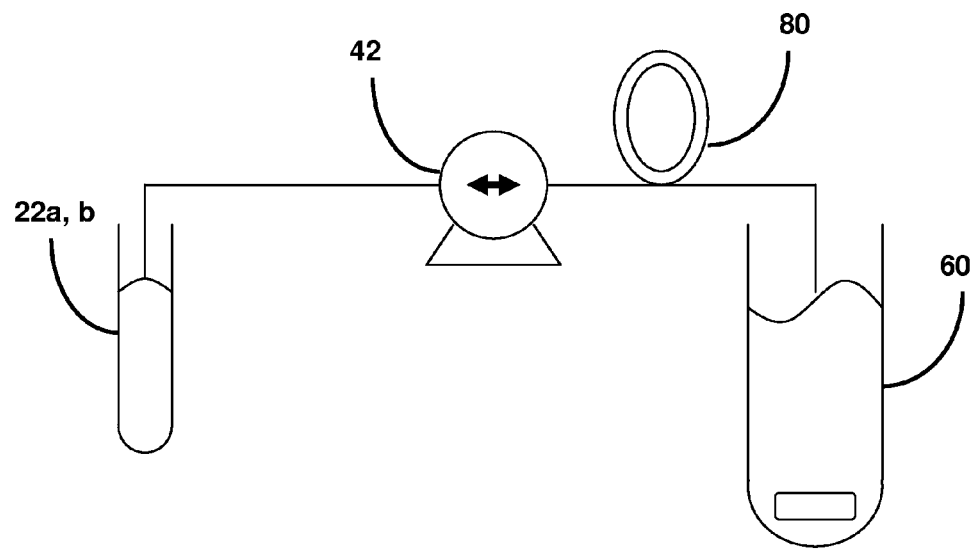

FIGS. 3a and 3b show preferred embodiments of the invention in which the samples that have been withdrawn or taken are conveyed directly to an analytical instrument, with FIG. 3a schematically showing sample drawing by a photometer measuring cell 70 and FIG. 3b schematically showing sample loading of a sample loop 80 of a chromatography injection system. Sample drawing from the dissolution vessel 60 can be accomplished at the planned sampling time by the measuring cell 70 or sample loop 80, or the sample fraction can be delivered to the measuring cell 70 or sample loop 80 from the vials 22a,b at a later point in time.

Based on the embodiments described above, a person skilled in the art will recognize that additional advantageous embodiments can be realized on the basis of the sampler according to the invention. In addition, a person skilled in the art will recognize that the terms used herein, such as "above" or "downward," "front" or "back" and the like, are not intended to limit in any way the orientation of the elements according to the invention characterized in detail thereby, but instead serve merely to distinguish these elements from one another.

What is claimed is:

1. A sampler, for use in testing the dissolution behavior of pharmaceutical products, wherein the sampler comprises:
   a vial holder for accommodating a plurality of vials:
   a sampling needle assembly with a plurality of sampling needles, wherein the sampling needle assembly and the vial holder may be moved relative to one another in such a way that the sampling needles of the sampling needle assembly may be inserted into the vials of the vial holder; and a pump unit with a plurality of diaphragm pumps which are designed to convey a fluid via the sampling needle assembly to the vials in the vial holder and to withdraw a fluid therefrom;
   wherein the diaphragm pumps have one controllable valve each at their fluid inlet and their fluid outlet so that bidirectional fluid transport can take place;
   wherein the controllable valves are designed such that the diaphragm pumps can be operated in accordance with the FIFO principle.

2. The sampler according to claim 1, wherein the controllable valves are solenoid valves.

3. The sampler according to claim 1, wherein the sampler additionally comprises a control unit that is designed to move the sampling needle assembly and the vial holder relative to one another, and to control the diaphragm pumps of the pump unit.

4. The sampler according to claim 1, wherein the control unit is designed to move the sampling needle assembly and the vial holder relative to one another in such a way that, as the vials of the vial holder are filled, the tips of the sampling needles in the sampling needle assembly follow the liquid level in the vial.

5. The sampler according to claim 1, wherein the cuvettes of a photometer are connected to the lines from the dissolution vessel to the diaphragm pumps.

6. The sampler according to claim 1, wherein the sample loops of a chromatography injection system are connected to the lines from the dissolution vessel to the diaphragm pumps.

* * * * *